United States Patent  [19]
Allen et al.

[11] Patent No.: US 6,281,971 B1
[45] Date of Patent: Aug. 28, 2001

(54) METHOD FOR ADJUSTING SPECTRAL MEASUREMENTS TO PRODUCE A STANDARD RAMAN SPECTRUM

(75) Inventors: Fritz Schreyer Allen, Corrales; Jun Zhao, Albuquerque, both of NM (US)

(73) Assignee: New Chromex, Inc., Freeway, NM (US)

( * ) Notice: Subject to any disclaimer, the term of this patent is extended or adjusted under 35 U.S.C. 154(b) by 0 days.

(21) Appl. No.: 09/658,708

(22) Filed: Sep. 8, 2000

Related U.S. Application Data

(63) Continuation-in-part of application No. 09/313,905, filed on May 18, 1999, now Pat. No. 6,141,095.

(51) Int. Cl.⁷ .............................. G01J 3/44; G01N 21/65

(52) U.S. Cl. ............................................................. 356/301

(58) Field of Search ............................................. 356/301

(56) References Cited

PUBLICATIONS

Effective Rejection of Fluorescence Interference in Raman Spectroscopy Using a Shifted Excitation Difference Technique, A. P. Shreve, N. J. Cherepy, and R. A. Mathies, 46 Applied Spectroscopy 707 (1992).

Fluorescence Rejection in Raman Spectroscopy by Shifted–Spectra, Edge Detection, and FFT Filtering Techniques, P.A. Mosier–Boss, S. H. Lieberman, and R. Newberry, 49 Applied Spectroscopy 630 (1995).

A collection of abstracts from various magazines and journals, including, for example, the *Journal of American Chemical Society*, in which reference may have been made to the reference/article first identified above by Mathies, et al., and may have discussed principles of shifted excitation Raman difference spectroscopy. Please Note: Included as pp. 1–23 with this Information Disclosure Statement is a copy of the collection of abstracts.

A true and correct copy of *Semiconductor Diode Lasers vol. I*, edited by William Streifer and Michael Ettenberg, IEEE Press (1991).

Fluorescence Rejection in Raman Spectroscopy by Shifted–Spectra, Edge Detection, and FFT Filtering Techniques, P.A. Mosier–Boss, S. H. Lieberman, and R. Newberry, 49 Applied Spectroscopy 630 (1995).

*Primary Examiner*—F L Evans
(74) *Attorney, Agent, or Firm*—Ray R. Regan (57) ABSTRACT

A method for producing a standard Raman spectrum of a sample. A source of incident radiation is provided. Means provide an incident beam and a monitor beam from the incident radiation. The incident beam is directed to the sample and a Raman beam is generated from the sample. Spectral data may be collected directly from the monitor beam and the Raman beam simultaneously. The occurrence of a frequency shift in the incident radiation is determined. One spectral measurement is made after the occurrence of the frequency shift, or a first spectral measurement is made before and a second spectral measurement is made after the frequency shift. One or more arithmetic calculations are applied to the single spectral measurement, or the second spectral measurement is subtracted from the first spectral measurement. One or more integral transforms are applied to the resulting spectral measurement data to produce the standard Raman spectrum.

37 Claims, 7 Drawing Sheets

METHOD FOR ADJUSTING SPECTRAL MEASUREMENTS TO PRODUCE A STANDARD RAMAN SPECTRUM

CROSS-REFERENCE TO RELATED APPLICATION

Applicants claim priority in this continuation-in-part patent application based on United States patent application filed in the United States Patent and Trademark Office on May 18, 1999, application Ser. No. 09/313,905 ("Parent Application"), which issued on Oct. 31, 2000 to Allen, et al., as U.S. Pat. No. 6,141,095 ("Allen Patent").

FIELD OF THE INVENTION

The present invention pertains generally to the field of spectroscopy. More particularly, the present invention pertains to an apparatus and method for adjusting spectral measurements to achieve a standard Raman spectrum. The present invention is particularly, but not exclusively, novel and useful for determining a standard Raman spectrum by adjusting spectral measurements affected by one or more frequency shifts.

BACKGROUND OF THE INVENTION

Spectroscopy is a general term for the process of measuring energy or intensity as a function of wavelength in a beam of light or radiation. Many conventional spectroscopes, and components comprising a spectroscope system, also referred to as an instrument, may include basic features and components such as a slit and a collimator for producing a parallel beam of radiation, one or more prisms or gratings for dispersing radiation through differing angles of deviation based on wavelength, and apparatus for viewing dispersed radiation. Spectroscopy uses absorption, emission, or scattering of electromagnetic radiation by atoms, molecules or ions to qualitatively and quantitatively study physical properties and processes of matter.

Light or radiation directed at a target, or sample of physical matter, during operation of a spectroscope system may be referred to as incident radiation. Redirection of incident radiation following contact with a sample of physical matter ("sample") commonly is referred to as scattering of radiation. To the extent that atoms or molecules in a sample absorb all or a portion of incident radiation, rather than reflect incident radiation, a sample may become excited, and the energy level of the sample may be increased to a higher energy level. Electromagnetic radiation, including incident radiation, that passes through a sample, may produce a small portion of light that is scattered in a variety of directions. Light that is scattered but continues to have the same wavelength as the incident radiation will also have the same energy, a condition often referred to as Rayleigh or elastically scattered light. Incident radiation that is scattered during a change of vibrational state in molecules may be scattered with a different energy, and such scattered light may be called Raman scattered light. Such phenomena have been used in conjunction with spectroscopy to qualitatively and quantitatively study physical properties and processes, including identification of chemical properties, compositions, and structures of a sample.

A wave associated with electromagnetic radiation may be described by wavelength, the physical length of one complete oscillation, and by frequency of the wave, the number of oscillations per second that pass a point. If incident radiation is directed at a sample, the wavelength of the incident radiation may remain substantially unchanged in scattered radiation. Alternatively, if incident radiation is directed at a sample, the wavelength in the scattered radiation may acquire one or more different wavelengths than the incident wavelength. The energy differential between the incident radiation and the scattered radiation may be referred to as a Raman shift. Spectroscopic measurement of Raman scattered light seeks in part to measure the resulting wavelength of such scattered light.

Raman scattered light may occur at wavelengths shifted from the incident light by quanta of molecular vibrations. The phenomenon of Raman scattered light, therefore, is useful in spectroscopy applications for studying qualities and quantities of physical properties and processes, including identification of chemical properties, compositions, and structure in a sample. Currently, Raman shift spectroscopic analytical techniques are used for qualitative and quantitative studies of samples. If incident radiation is used to scatter light from a sample, and scattered radiation data is measured, the scattered radiation may provide one or more frequencies associated with the sample, as well as the intensities of those shifted frequencies. The frequencies may be used to identify the chemical composition of a sample. If, for example, intensities are plotted on a Y-axis, and frequency or frequencies are plotted on an X-axis, the frequency or frequencies may be expressed as a wave number, the reciprocal of the wavelength expressed in centimeters. The X-axis, showing frequency or frequencies, may be converted to a Raman shift in wave numbers, the measure of the difference between the observed wave number position of spectral bands, and the wave number of radiation appearing in the incident radiation.

While these principles and phenomena are known, until recently efforts to apply the principles and phenomena to qualitative and quantitative analyses of samples have not always resulted in uniform, predictable results, or in acceptable levels of precision and accuracy of Raman spectra. Because of instrumentation variabilities, inherent weakness of a Raman scattered signal, fluorescence, and other limitations associated with spectroscopy instruments, the goal of producing a standard Raman spectrum for use in sample analyses was, until recently, a challenge not achieved by apparatus and methods known in the art.

At least one problem that had to be overcome was the fact that spectroscopic measurements of Raman scattered light seeking to measure wavelength or intensities, or both, of scattered light, could be affected by the instrument, or spectroscopic system, itself. A number of components of an instrument may contribute individually and collectively to undesirable instrumentation variabilities that affect spectral data measured by the instrument. Raman scattered radiation from a sample may be observed, measured, and directed through an instrument by optics of a spectrometer, may be coded by a device such as an interferometer, and may be directed to one or more detectors to record Raman spectra. Any one, or all, of such components of a conventional spectrometer system induced or contributed to instrumentation variabilities that reduced or adversely affected the precision and accuracy of measurements of Raman scattered light.

In addition to fluorescence, spectral measurements of a source of incident radiation such as a laser, including semiconductor or diode lasers, will evidence other varying baseline components, artifactual or real, that preferably could be eliminated, suppressed, or compensated for to provide an accurate Raman spectrum for analytical purposes. In instrumentation designs preferred by users of Raman technology, semiconductor diode lasers would be the choice of incident radiation due to small and compact sizing, low heat dissipation, and high energy conversion efficiency. Use of semiconductor or diode lasers, while useful because of a number of important characteristics, also engender unique problems that, if solved, would advance Raman technology. However, at least one other problem associated with semiconductor diode lasers is the tendency for the output to change from one frequency to another during operation, commonly referred to as frequency drift. Frequency drift is generally related to temperature variations that may cause either slow frequency drifts or drastic frequency changes. Semiconductor diode lasers also are susceptible to mode hops when the laser switches output from one frequency to a new preferred frequency.

Some of the problems associated with frequency shifts were discussed as early as 1991 in *Semiconductor Diode Lasers Volume I*, edited by William Streifer and Michael Ettenberg, IEEE Press (1991), a work incorporated by reference into this document. In general, frequency shifts, or mode hops, are inherent in laser light, and can be eliminated only by redesigning the laser at excessive cost. Solutions for overcoming the effects of frequency shifts have included redesign of the internal cavity of lasers, designing what is known as an external cavity for lasers, and tuning a range of modes into a single mode. All of those solutions are achieved at considerable expense, and generally shorten the useful life of a semiconductor laser. A further problem related to diode lasers includes variations in output intensity that directly affect the measured Raman shift. Rather than eliminate the problem physically, which is expensive and limits the effective life of the laser, it would also be useful to compensate for the frequency shifts and intensity variabilities. Thus, it is at least an objective of the present invention to overcome problems associated with using excitation sources in the visible range of light, including, for example, removal of fluorescence and other common mode noise from acquired spectra.

Fortunately, in the Allen Patent, problems arising from instrumentation variabilities, including issues in connection with the use of semiconductor lasers, were overcome. The Allen Patent, incorporated by reference into this document as if fully set forth herein verbatim, discloses and claims an apparatus for measuring and applying instrumentation correction to produce a standard Raman spectrum. It would be novel and useful, however, to use the apparatus of the Allen Patent in a novel and unique way to provide a standard Raman spectrum by addressing primarily phenomena associated with sample interferences including common mode background interferences. To appreciate that contribution to Raman technology presented by the present invention, however, it is useful to review some perplexities of Raman phenomena.

Raman scattering is a comparatively weak effect when compared with Rayleigh or elastic scattering. Nevertheless, Raman scattering offers a significant opportunity for qualitative and quantitative studies of physical properties and processes, including identification of chemical compositions and structure in samples of physical matter. To appreciate these phenomena, as well as understand the problems solved by the present invention, it should be noted that depending on the compound comprising a sample, only about one scattered photon in $10^{6-8}$ tends to be Raman shifted. Because Raman scattering, therefore, is such a comparatively weak phenomenon, an instrument used to disperse radiation for measurement purposes should have minimal stray light and be able to substantially reject Rayleigh scattering; otherwise, a Raman shift may not be measurable.

As earlier described, Raman phenomena result in spectral information that is shifted relative to the excitation source, or source of incident radiation. Thus, any variations in the excitation source will result in a relative change, or shift, in spectral information. Spectrally shifted Raman information also is directly related to the intensity of the excitation source. A further complication arises from multiple lines in the frequency of the source of incident radiation that may cause shifted, multiple sets of spectra from a sample. Therefore, conventional Raman experimentation discloses that a source or sources of incident radiation that causes or cause excitation in a sample used in connection with a spectrograph should be substantially monochromatic, preferably providing a single frequency or wavelength. Recognition that the source of incident radiation requires a substantially monochromatic frequency has led to use of a variety of laser light sources as a source of incident radiation because of the substantially monochromatic frequency and high intensity of a laser. Gas lasers such as helium-neon, helium-cadmium, argon-ion, krypton-ion, as well as solid state lasers including Nd-YAG, and diode lasers, solid state tunable lasers, liquid dye lasers, and other lasers, have been used.

Preferably, a source of incident radiation would provide a substantially monochromatic frequency and radiation closer to the blue portion of the visible light spectrum providing short wavelength excitation because the Raman effect is enhanced by use of short wavelength excitation, and because of the enhanced quantum efficiency ("QE") of charged coupled detectors ("CCD's") in use today.

An undesirable result of incident radiation on a sample occurs if a sample generates red shifted radiation as part of a radiation absorption process, a phenomenon commonly referred to as fluorescence. Fluorescence occurs when absorbed radiation is lowered in frequency by internal molecular processes and emitted as radiation that is closer to the red end of the visible light spectrum. Fluorescence sometimes may be strong enough in comparison with the Raman shift to swamp, or substantially eliminate, the weaker Raman signal. Fluorescence is a major interference for samples using excitation wavelengths in the visible region of the light spectrum, and has therefore made use of blue and green excitation sources problematic. Using excitation sources in the far end of the red end of the light spectrum mitigates the fluorescence effect, however, particularly in connection with silicon detectors, but substantially restricts use of instrument components that tend to provide radiation far into the infrared ("IR") region of the light spectrum.

In one embodiment of the present invention, therefore, the apparatus collects a first spectral measurement from the incident beam and a first spectral measurement from the Raman beam. One or more frequency shifts are quantified, namely induced, identified and measured. Following the step of quantifying one or more frequency shifts, either induced or naturally occurring, the apparatus collects second spectral data from the incident beam and second spectral data from the Raman beam. Using the apparatus for measuring and applying instrumentation correction, spectral data modifications are applied to the resultant spectral data. As used in this document, the term "spectral data modifications" may include scaling, if necessary, where scaling includes one or more mathematical procedures for correcting ratio imbalances well known to those skilled in the art. The term "spectral data modifications" also includes a subtraction step in connection with the obtained spectral data. In addition, one or more integral transforms are applied to the respective spectral data. The resultant data then is deconvolved to produce the standard Raman spectrum of the sample.

In another embodiment of the present invention the standard Raman spectrum of a sample is obtained using a single spectrum. The apparatus collects a first spectral measurement set from the incident beam and Raman beam. The spectral measurement set frequency axis is shifted, and one or more shifted, spectral data set is collected. The alternative embodiment also applies one or more spectral data modifications to the spectral measurement set and to the one or more shifted spectral data sets to produce the standard Raman spectrum of the sample. One or more means for correcting spectral data, well known to those skilled in the art, may be used if necessary to flatten the baseline data to produce the standard Raman spectrum of the sample. The one or more means for correcting spectral data may include linearizing the spectral data; subtracting a spline, polynomial or other function; one or more pattern recognitions; Fourier filtering; or smoothing to reveal the details of the result, as well as one or more other methods well known in the art.

Earlier efforts to provide a fluorescence rejection technique were suggested in Effective Rejection of Fluorescence Interference in Raman Spectroscopy Using a Shifted Excitation Difference Technique, A. P. Shreve, N. J. Cherepy, and R. A. Mathies, 46 *Applied Spectroscopy* 707 (1992) ("Mathies Reference"), and Fluorescence Rejection in Raman Spectroscopy by Shifted-Spectra, Edge Detection, and FFT Filtering Techniques, P. A. Mosier-Boss, S. H. Lieberman, and R. Newberry, 49 *Applied Spectroscopy* 630 (1995) ("Lieberman Reference"). By those skilled in the art, it is recognized that fluorescence is a broad band spectral phenomena; small changes in frequency of the excitation source have little if any effect on the spectrum. This is not true of Raman phenomena, where small changes in excitation source frequency correspond to a similar change in the Raman shifted spectrum relative to the excitation source.

The Mathies Reference suggests obtaining a first spectra reading that includes a Raman reading and fluorescence reading, moving the laser to a shorter excitation frequency, and obtaining a second spectra that was subtracted from the first spectra. The author suggested that the resultant difference spectra would remove the broad band fluorescence spectrum, leaving only Raman shifted information. The resulting difference spectrum was fit in a non-linear least square process with sets of difference functions for each peak as determined by inspection of graphs of the different spectra, and a conventional spectrum was reconstructed using modeling techniques.

While the ideas of the Mathies Reference conceptually are useful, the apparatus and methods recommended included a number of problems. The shift in frequency of the excitation source must be known precisely, a requirement that led to use of a tunable laser. Tunable lasers are complex, bulky, and expensive. The output frequency of a tunable laser is assumed to remain stable, at a known frequency, during an entire integration time. If the frequency were to change during operation, the method proposed by the Mathies Reference would not work. Further, changes in output power of a tunable laser during sample integration time was unacceptable because of concern that the signal would scale with laser power, and cancellation of fluorescence would be incomplete. The Mathies Reference also poses a number of other problems associated with data interpretation, including the fact that a first approximation or estimate must be made for band centers, areas, and standard deviations of the difference spectra. An iterative non-linear least squares process then must be used to refine the first approximations to generate a best fit to the differential data. Further, the data analyses method of the Mathies Reference requires substantial and significant knowledge about the sample, including how many Raman bands are present in the spectrum. For each of the features, one must be able to make reasonable first approximations of the parameters fitted by an optimization routine, a process making it increasingly difficult to determine band areas and standard deviations for complex compounds. The Mathies Reference also makes use of a sample with only three Raman bands; more complex samples will exacerbate the limitations with this approach. Finally, the end result is not a measured result, but rather a modeled one, which limits its acceptance for certain applications such as forensic and FDA related applications.

The Lieberman Reference suggests use of a technique for using the shifted excitation Raman difference method of the Mathies Reference, but instead shifts either the spectrometer settings prior to collection of a second spectrum, or artificially shifts the digitized spectrum of the first acquisition. While this approach does not require a tunable laser beam source, it has all the limitations of the Mathies approach.

What is needed, therefore, is an apparatus in combination with a novel and useful spectra data analysis method that will overcome existing problems associated with implementing shifted excitation Raman difference spectroscopy. The need for such a method is evident because suppression of sample fluorescence, or other common mode interferences that are not effected by small changes in excitation source frequency, offers significant advantages. A method using an apparatus for adjusting spectral measurements to mitigate effects of fluorescence, and to produce a standard Raman spectrum, would allow measurements not only in the red or infrared spectrum of light, as is now commonly imposed by the nature of Raman technology, but also in the blue and green region. Maximum advantage could be achieved by using the green portion of the light spectrum, where the CCD (charge coupled devices) are most efficient. Inexpensive, unstabilized semiconductor diode lasers could be used. Modeling, or special understanding of differential data, would be unnecessary.

A number of problems must be solved to achieve the goal of providing a method for adjusting Raman spectra to produce a standard Raman spectrum using the concept of shifted excitation Raman differences to suppress or compensate for fluorescence and other common mode interferences that are not affected by small changes in the excitation source frequency. What is needed to solve the problems is a method for using an apparatus that is useful not only for measuring and applying instrumentation correction to produce a standard Raman spectrum, as provided in the Allen Patent, but also useful for inducing and monitoring a frequency shift at the user's direction. The apparatus should be capable of making one or more spectral measurements after occurrence of the frequency shift. The apparatus and method also should include ways to apply one or more arithmetic calculations to either a single spectral measurement, or to obtain a positive result in the nature of resulting spectral measurement data from subtracting a second spectral measurement from a first spectral measurement. The apparatus should allow application of one or more integral transforms to the resulting spectral measurement data to produce the standard Raman spectrum of the sample. The apparatus and method should be fully automated, relieving an operator of the apparatus from being either skilled in the art or possessing special skills, yet being capable of maintaining the quality of the data over a time period unmonitored or unattended by an operator of the system. In addition, high resolution Raman spectra should be achieved using an apparatus and method of operation of the apparatus that is easy to use, predictably accurate, easy to practice, and relatively cost effective.

One of many advantages of the new and useful present invention, therefore, is a method useful in adjusting spectral measurements occasioned by sample interferences to produce a standard Raman spectrum of the sample. The present invention, therefore, is useful in inducing and determining the occurrence of a frequency shift in the incident radiation and Raman radiation. The apparatus is capable of making one or more spectral measurements after occurrence of the frequency shift. The apparatus also is capable of making a first spectral measurement before the frequency shift and a second spectral measurement after the frequency shift. One or more arithmetic calculations, well known to those skilled in the art, are applied to the single spectral measurement to obtain a spectral measurement. Alternatively, the second spectral measurement may be subtracted from the first spectral measurement. The apparatus allows application of one or more integral transforms to the resulting spectral measurement data to produce the standard Raman spectrum of the sample. The apparatus and method are fully automated. In addition, the apparatus and method are easy to use, predictably accurate, easy to practice and are cost effective.

These advantages and other features of an apparatus and method for adjusting spectral measurements to produce a standard Raman spectrum will become apparent to those skilled in the art when read in conjunction with the accompanying following description, drawing figures, and appended claims.

SUMMARY OF THE INVENTION

An apparatus for adjusting spectral measurements to produce a standard Raman spectrum of a sample, according to the present invention, includes a source of incident radiation. The source of incident radiation provides substantially monochromatic radiation or light. A source of incident radiation, therefore, may include a laser. A variety of laser light sources may be used in connection with the present invention not only because of the substantially monochromatic nature of the radiation, but also because of the high intensity of laser radiation.

A method for adjusting spectral measurements to produce a standard Raman spectrum of a sample, also includes one or more means for providing from the incident radiation an incident beam and a monitor beam. A means for providing an incident beam and a monitor beam is installation of one or more wave guides, such as a beam splitter waveguide, in the path of the incident radiation. The incident beam is directed at the sample to be analyzed. The incident beam induces or generates scattered radiation on contact with the sample. The scattered radiation has an energy differential different from, and one or more wavelengths different than, the incident radiation, comprising the Raman shift. For convenience, the Raman shift is described in this document as a Raman beam to be analyzed by the instrument.

The incident beam and the Raman beam may pass through a variety of instrumentation components during operation of the instrument. The arrangement and combination of instrument structural components, however, provided in connection with the present invention, are not determinative of the capability of the present invention to achieve superior precision and accuracy in connection with the measurement of a standard Raman spectrum, instrument independence, and elimination of the need for ideal excitation frequency stability. Thus, the Raman beam and incident beam may be directed to one or more wave guides, optics, reflectors, mirrors, focusing lenses and filters. The present invention may also include one or more sources of white light for imparting instrument response or shape correction to the Raman beam, as well as means for adding a frequency calibration standard to the instrument. Likewise, the present invention may include a variety of instrumentation components for collecting monitor beam spectral data. As is true of the Raman beam, the precise arrangement and combination of structural components is not determinative of the ability of the present invention to achieve superior precision and accuracy in connection with the measurement of a standard Raman spectrum, as well as instrument independence, while eliminating the need for ideal excitation frequency stability. The monitor beam, for example, may be directed from a waveguide through one or more devices for imparting to the monitor beam a frequency calibration.

Also provided in connection with the present invention are means for inducing and measuring the occurrence of frequency shifts in the incident radiation and Raman radiation. The method of the present invention uses an apparatus capable of making one spectral measurement after occurrence of a frequency shift. The apparatus also is capable of making a first spectral measurement before a the frequency shift and a second spectral measurement after a frequency shift. One or more spectral data modifications may be applied to the spectral data to determine the standard Raman spectrum of the sample. For example, scaling may be applied to the spectral data if necessary. One or more arithmetic calculations well known to those skilled in the art may be applied to the single spectral measurement to obtain a spectral measurement. Alternatively, the second spectral measurement may be subtracted from the first spectral measurement. One or more integral transforms is applied to the resulting spectral measurement data to produce the standard Raman spectrum of the sample.

The Raman beam and monitor beam also are directed to one or more detectors. The one or more detectors contribute to collecting and displaying the spectral data of the incident wavelength of the monitor beam, and in determining intensity of the monitor beam, substantially simultaneously with establishment of the Raman radiation from the incident beam. To achieve the superior precision and accuracy of Raman spectra resulting from the present invention, however, a number of different means may be used. The monitor beam may be measured in any number of ways, and at any number of points, after the incident radiation is divided into a incident beam and a monitor beam. The instrumentation components may be arranged in the instrument to achieve collection of spectral data substantially simultaneously from the monitor beam and the Raman beam.

In addition, substantially simultaneous data measurements allows the incident beam frequency, or excitation frequency, to be shifted between spectral acquisitions, leading to the ability to perform shifted excitation Raman difference spectroscopy. This achieves the benefit of reducing or eliminating effects of fluorescence and other common mode structures that are not greatly affected by small changes in excitation frequency. Therefore, compounds that previously were difficult if not impossible to investigate by Raman technology are now more likely to be correctly evaluated using Raman spectroscopy. Additionally, the present invention provides the ability to substantially simultaneously perform data measurements of the incident beam source, or excitation source, as well as not simultaneously (sequentially) perform data measurements of the incident beam, and the Raman beam, in conjunction with the ability to induce changes in the excitation frequency, allowing application of shifted excitation Raman difference spectroscopy, and further allowing use of the green portion of the visible light spectrum in more compound analyses, thus greatly enhancing the sensitivity of the Raman effect. The ability to perform substantially simultaneous data measurements of the excitation source and Raman beam allow use of arithmetic calculations, integral transforms and deconvolution to be applied to the shifted excitation Raman difference spectrum.

As disclosed in this document, an integral transform refers to one or more calculations and processes by which the present invention compensates for undesirable Raman effects attributable to less than ideal characteristics of the source of incident radiation, including frequency and intensity instability. An integral transform, according to the present invention, may also include methods and calculations associated with autocorrelation. Substantially simultaneous spectral data collection in connection with integral transforms, in conjunction with the components of the apparatus, combine to provide high resolution Raman spectra that are not dependent on frequency stability in the source of incident radiation, and are independent of intensity fluctuations associated with the source of incident radiation. In addition, substantially simultaneous data measurements also allows user interchangeability of sample spectra among a number of spectrometers and similar apparatus because instrument variabilities are rendered irrelevant. As will be recognized by those skilled in the art, a computer or similar device may be used in conjunction with the apparatus for applying, and displaying the results of application, of the one or more integral transforms to the spectral measurements and to the resulting spectral measurement data.

The foregoing has outlined broadly the more important features of the invention to better understand the detailed description which follows, and to better understand the contribution of the present invention to the art. Before explaining at least one embodiment of the invention in detail, it is to be understood that the invention is not limited in application to the details of construction, and to the arrangements of the components, provided in the following description or drawing figures. The invention is capable of other embodiments, and of being practiced and carried out in various ways. Also, the phraseology and terminology employed in this disclosure are for purpose of description, and should not be regarded as limiting.

As those skilled in the art will appreciate, the conception on which this disclosure is based readily may be used as a basis for designing other structures, methods, and systems for carrying out the purposes of the present invention. The claims, therefore, include such equivalent constructions to the extent the equivalent constructions do not depart from the spirit and scope of the present invention. The abstract associated with this disclosure is neither intended to define the invention, which is measured by the claims, nor intended to be limiting as to the scope of the invention in any way.

The novel features of this invention, and the invention itself, both as to structure and operation, are best understood from the accompanying drawing, considered in connection with the accompanying description of the drawing, in which similar reference characters refer to similar parts, and in which:

DESCRIPTION OF THE PREFERRED EMBODIMENTS

Figure 1:
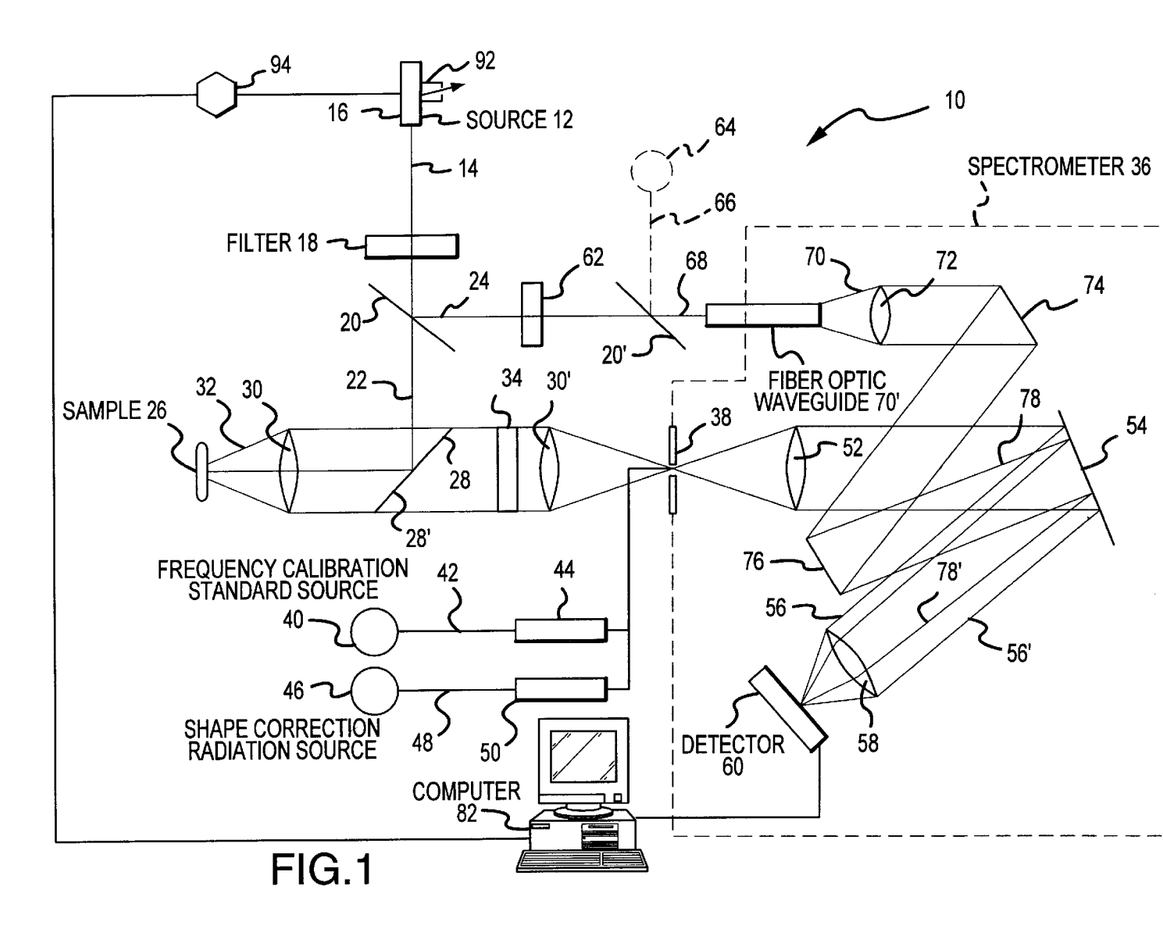
FIG. 1 is a schematic drawing of an apparatus for adjusting spectral measurements to produce a standard Raman spectrum of a sample according to the present invention.

Referring initially to FIG. 1, an apparatus for adjusting spectral measurements to produce a standard Raman spectrum is shown schematically, and generally designated 10. As also shown, an apparatus for adjusting spectral measurements to produce a standard Raman spectrum 10 includes a source 12 of incident radiation 14. Source 12 of incident radiation 14 provides incident radiation 14 in the form of a substantially monochromatic radiation or light. Source 12 of incident radiation 14, therefore, may be a laser 16. A variety of laser light sources may be used as laser 16 in connection with the present invention not only because of the substantially monochromatic nature of the radiation, but also because of the high intensity of laser radiation. In a preferred embodiment of the present invention, laser 16 is a semiconductor or diode laser that has not been frequency stabilized.

As also shown in FIG. 1, the present invention includes a filter 18. In the preferred embodiment of the present invention, filter 18 is a band-pass filter for narrowing wavelengths of incident radiation 14, and for removing undesirable radiation from incident radiation 14. The present invention also includes a waveguide 20 for providing from incident radiation 14 an incident beam 22 and a monitor beam 24 to enable the present invention to direct incident beam 22 at a sample 26 to be analyzed. Filter 18 may be located in the path of incident radiation 14 anywhere in the instrument before sample 26. And, although in a preferred embodiment waveguide 20 is a beam-splitter waveguide, a different waveguide 20 may be used in an alternative embodiment depending on the sensitivity of the instrument and the intensity of source 12 of incident radiation 14. Waveguide 20 also may include one or more prisms, partially silvered mirrors, and plate type beam splitters.

As stated, and as shown in shown in FIG. 1, an apparatus for adjusting spectral measurements to produce a standard Raman spectrum of sample 26 also includes a waveguide 20 for providing from incident radiation 14 an incident beam 22 and a monitor beam 24 to enable the present invention to direct incident beam 22 at a sample 26 to be analyzed. In a preferred embodiment of the present invention, monitor beam 24 represents a substantially smaller percentage of incident radiation 14 as compared with incident beam 22. In a preferred embodiment of the present invention, monitor beam 24 includes approximately one percent (1%) of incident radiation 14, and incident beam 22 includes the balance of incident radiation 14. The approximate ratio of 1:99 between radiation included, respectively, in monitor beam 24 and incident beam 22 is not, however, a limitation of the present invention.

The present invention also includes, as shown in FIG. 1, means for directing incident beam 22 at sample 26. Incident beam 22 may be directed at sample 26 without any intervening instrument components being located in the path of incident beam 22. Incident beam 22 also may be directed at a mirror 28. In a preferred embodiment of the present invention, mirror 28 is a dichroic mirror 28'. However, in an alternative embodiment of the present invention, an holographic transmissive element, or a mirror formed with a hole in the mirror may be used instead of dichroic mirror 28'. Thereafter, incident beam 22 may be directed through a lens 30. In a preferred embodiment of the present invention, lens 30 is a focusing lens in the path of incident beam 22 before incident beam 22 contacts sample 26. In another embodiment of the present invention, more than one lens 30 may be located in the path of incident beam 22 before incident beam 22 contacts sample 26.

Figure 1A:
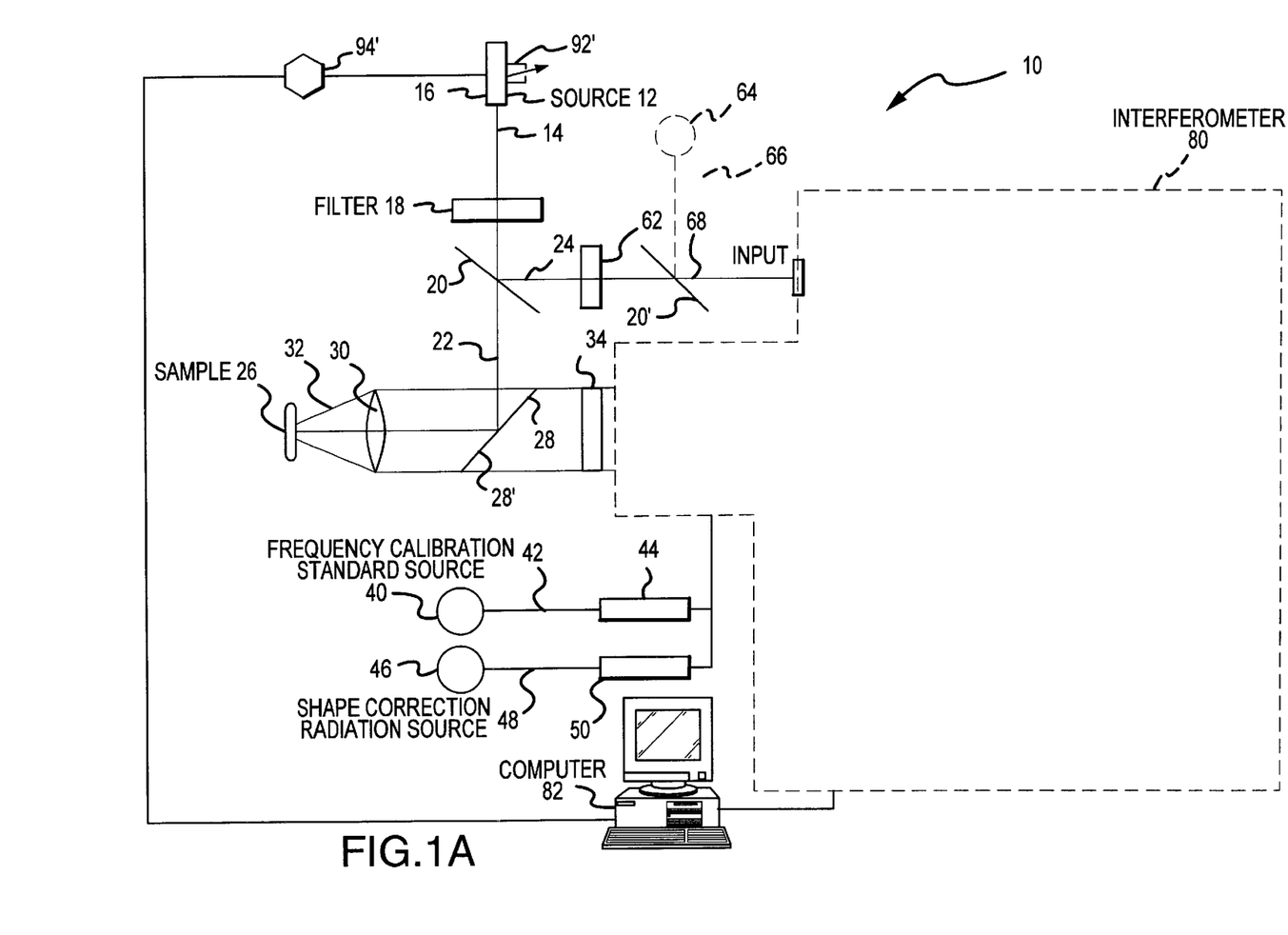
FIG. 1A is a schematic drawing of an alternative embodiment of an apparatus for adjusting spectral measurements to produce a standard Raman spectrum of a sample according to the present invention.

As also shown by reference to FIG. 1, incident beam 22 induces or generates on contact with sample 26 scattered radiation having an energy differential different from, and one or more wavelengths different than, incident radiation 14, or the Raman shift that, for convenience, is described in this document as a Raman beam 32. As stated, and as shown in FIG. 1, in a preferred embodiment of the present invention, a mirror 28, preferably a dichroic mirror 28', is provided. Raman beam 32 is directed back through lens 30 and dichroic mirror 28' in a 180 degree back-scatter geometry. Neither incident beam 22 nor Raman beam 32 need be co-linear. In the preferred embodiment of the present invention, however, Raman beam 32 passes back through dichroic mirror 28', then through a filter element 34, and then through a lens 30', preferably a focusing lens. Filter element 34 is, in the preferred embodiment, a long-pass filter. In an alternative embodiment of the present invention, filter element 34 is a notch filter, or any other filter that is capable of rejecting elastically scattered radiation. Raman beam 32 is, as shown in FIG. 1, positioned to enter spectrometer 36 (shown by dashed lines) through slit 38. As previously stated, however, Raman scattered radiation from a sample, such as sample 26, may be coded by a device such as an interferometer. In an alternative embodiment of the present invention, therefore, Raman beam 32 is, as shown in FIG. 1, is positioned to enter an interferometer as shown in FIG. 1A.

The present invention also includes one or more means for imparting a frequency calibration standard to the instrument and for imparting shape correction to Raman beam 32. In a preferred embodiment of the present invention, a frequency calibration standard source 40 provides a frequency calibration beam 42. Frequency calibration beam 42 is directed into spectrometer 36 using a first fiber optic waveguide 44. Frequency calibration beam 42, preferably a neon light source, may be introduced into the instrument at slit 38 of spectrometer 36, where Raman beam 32 also enters spectrometer 36. Frequency calibration provided by frequency calibration source 40 contributes to compensation for instrumentation variabilities because spectral data of a known standard maybe compared with spectral data of Raman beam 32. The present invention also includes a shape correction radiation source 46 that provides a shape correction beam 48. Shape correction radiation source 46 is, in the preferred embodiment of the present invention, a white light source. In an alternative embodiment of the present invention, shape correction radiation source 46 may be a broad band fluorescent or phosphorescent source. Shape correction beam 48 is directed into spectrometer 36 using a second fiber optic waveguide 50. Shape correction beam 48 may be introduced into the instrument at slit 38 of spectrometer 36, where Raman beam 32 also enters spectrometer 36.

Referring again to FIG. 1, and to the positioning of Raman beam 32 at the entrance to spectrometer 36 at slit 38, the present invention also includes a second lens 52 located within spectrometer 36. In a preferred embodiment of the present invention, second lens 52 is a focusing lens for focusing Raman beam 32 toward a first dispersive grating 54. First dispersive grating 54 separates wavelengths of Raman beam 32 to form a dispersed signal shown diagrammatically by lines 56 and 56' in FIG. 1. Also included in the present invention is a third lens 58 for focusing dispersed signal 56–56' on detector 60. In a preferred embodiment of the present invention, detector 60 is a charge coupled device. Also in a preferred embodiment of the present invention, detector 60 is capable of displaying on one or more pixel configurations on the same detector 60 data that is associated with frequency calibration beam 42 from frequency calibration standard source 40. Detector 60 also is capable of displaying on one or more pixel configurations on detector 60 data associated with shape correction beam 48 for determining the extent, if any, spectral data is affected by instrumentation variabilities. The same detector 60 also may display the monitor beam on a separate set of pixels or spatial channel. In an alternative embodiment of the present invention, detector 60 may be a multi-channel array detector, including as a nonexclusive example a photodiode array detector. In addition, the data may be viewed on one or more detectors 60, and a second spectrometer may be provided to view monitor beam 24.

As stated, an apparatus for adjusting spectral measurements to produce a standard Raman spectrum of a sample 10 also includes, as shown in FIG. 1, means for collecting spectral data substantially simultaneously from monitor beam 24 as well as from Raman beam 32. Monitor beam 24 is used to ascertain wavelength spectra and intensity of incident radiation 14. Wavelength spectra and intensity of incident radiation 14, according to the present invention, is collected substantially simultaneously with collection of spectral data in connection with Raman beam 32. Means for collecting spectral data substantially simultaneously from monitor beam 24 include a second filter 62 located in the path of monitor beam 24. In a preferred embodiment of the present invention, second filter 62 is an intensity filter. Second filter 62 is located in the path of monitor beam 24 to contribute to reduction of the intensity of source 12 of incident radiation 14. In an alternative embodiment of the present invention second filter 62 may be a diffuser. In another alternative embodiment of the present invention second filter 62 may be eliminated if detector 60 will not be so saturated as to affect deconvolution of the spectral data. Also shown diagrammatically is frequency calibration standard source 40 as second frequency calibration standard source 64. In a preferred embodiment of the present invention, second frequency calibration standard source 64 is a neon light source. In an alternative embodiment of the present invention, second frequency calibration standard source 64 may be an emitter having a stable frequency. Preferably, second frequency calibration standard source 64 provides a known wavelength or spectral data to contribute to comparing the wavelength of source 12 of incident radiation 14 with any shifts in source 12 of incident radiation 14. Second frequency calibration standard source 64 produces a second frequency calibration standard beam 66. Second frequency calibration standard beam 66 from second frequency calibration standard source 64 may be applied to monitor beam 24 at waveguide 20' located in the path of second frequency calibration standard beam 66 and in the path of monitor beam 24, as shown in FIG. 1. Second frequency calibration standard beam 66 may be superimposed on the same path as monitor beam 24. On application of a frequency calibration standard to monitor beam 24, the resulting combined monitor-calibration beam 68 results. The present invention also provides for a third waveguide 70 located in the path of combined monitor-calibration beam 68. In a preferred embodiment of the present invention, third waveguide 68 is a fiber optic waveguide 70'. Fiber optic waveguide 70' includes a fourth lens 72. Combined monitor-calibration beam 68 passes through fourth lens 72 to a turning mirror 74 that directs combined monitor-calibration beam 68 to a second dispersive grating 76, as shown in FIG. 1. Second dispersive grating 76 separates combined monitor-calibration beam 68 into different wavelengths, and provides added spectral resolution to combined monitor-calibration beam 68 before directing the resulting signal 78 and 78' to first dispersive grating 54 to be focused on detector 60. In an alternative embodiment of the present invention, dispersive grating 76 may be one or more prisms or holographic gratings.

Figure 6:
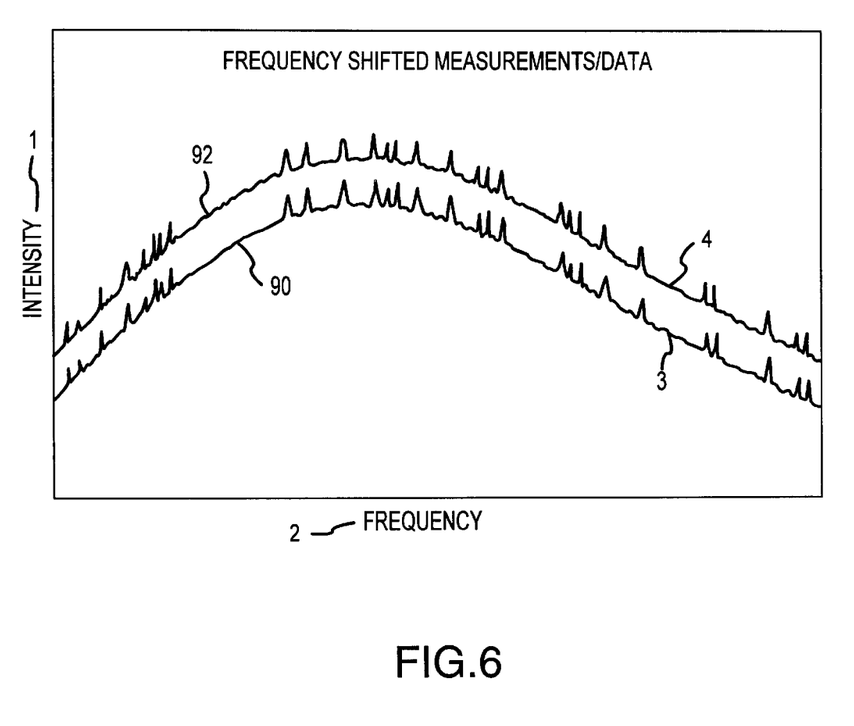
FIG. 6 is a graph showing the results after application of the invention for Raman spectra recovery from a large fluorescence background, where reference numeral "1" shows the intensity axis, "2" the frequency axis, "3" a first measurement, and "4" a second measurement and data set.
Figure 7:
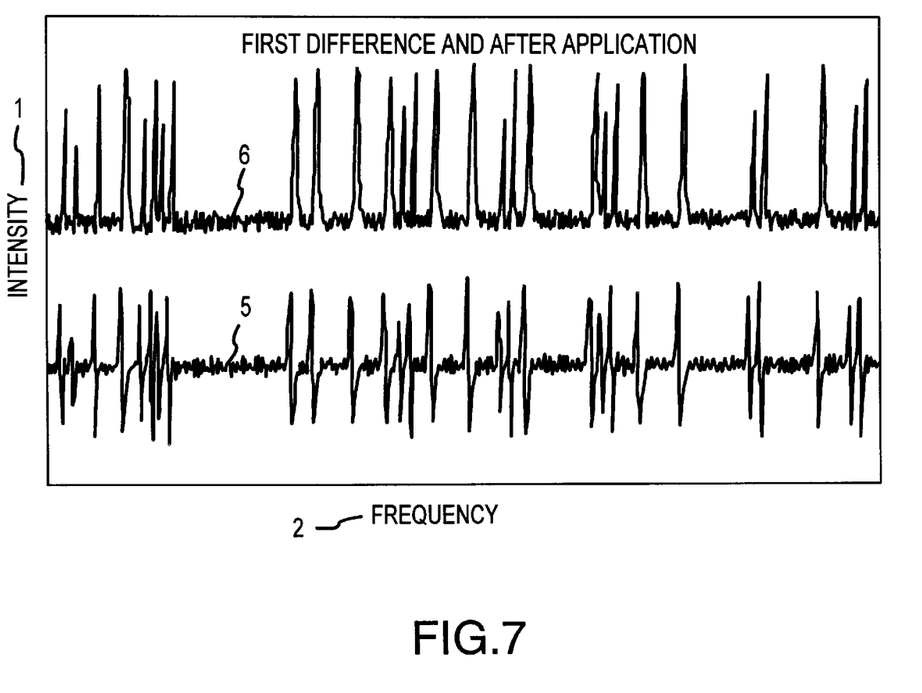
FIG. 7 is a graph showing application of the invention to produce, as shown by reference numeral "5," a first result, and by reference numeral "6" a standard Raman spectrum.
Figure 8:
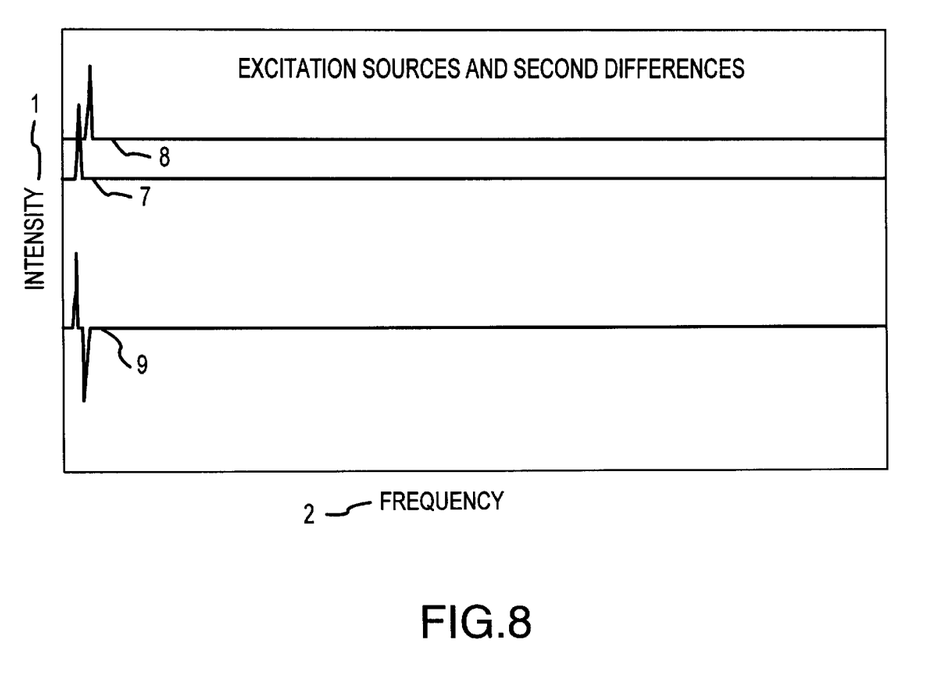
FIG. 8 is a graph showing the Raman source figures, wherein reference numeral "7" shows a first Raman beam, "8" a second Raman beam, and "9" the difference.

Also provided in connection with the present invention is a means for inducing occurrence of a frequency shift in incident radiation 14 and Raman beam 32, as best shown in FIG. 6. Apparatus 10 may make one spectral measurement after occurrence of a frequency shift. Apparatus 10 also is capable of making a first spectral measurement before a frequency shift and a second spectral measurement after a frequency shift. In a preferred embodiment of the present invention, the spectral measurements are made by apparatus 10 and displayed on a computer 82. In the preferred embodiment of the present invention the means for inducing the occurrence of a frequency shift in incident radiation 14 is at least switch 92, best shown in FIG. 1, that changes the temperature setting of laser 16. As will be recognized by those skilled in the art, inducing the occurrence of a frequency shift in incident radiation 14 may be caused by any number of alternative means 94, which may include using mathematical means. One or more arithmetic calculations may be applied to the single spectral measurement to obtain an adjusted spectral measurement. Alternatively the second spectral measurement may be subtracted from the first spectral measurement. Apparatus 10 allows application of one or more integral transforms to the resulting spectral measurement data to produce the standard Raman spectrum of the sample. In the preferred embodiment of the present invention, the second spectral measurement is subtracted from the first spectral measurement, and the second monitor beam measurement is subtracted from the first monitor beam measurement. One or more integral transforms are applied to the resulting difference spectra to produce the standard Raman spectrum of the sample, as shown best by reference to FIG. 7. FIG. 8 shows the Raman source figures, indicating that reference numeral "7" shows a first Raman beam, "8" a second Raman beam, and "9" the difference.

Figure 2:
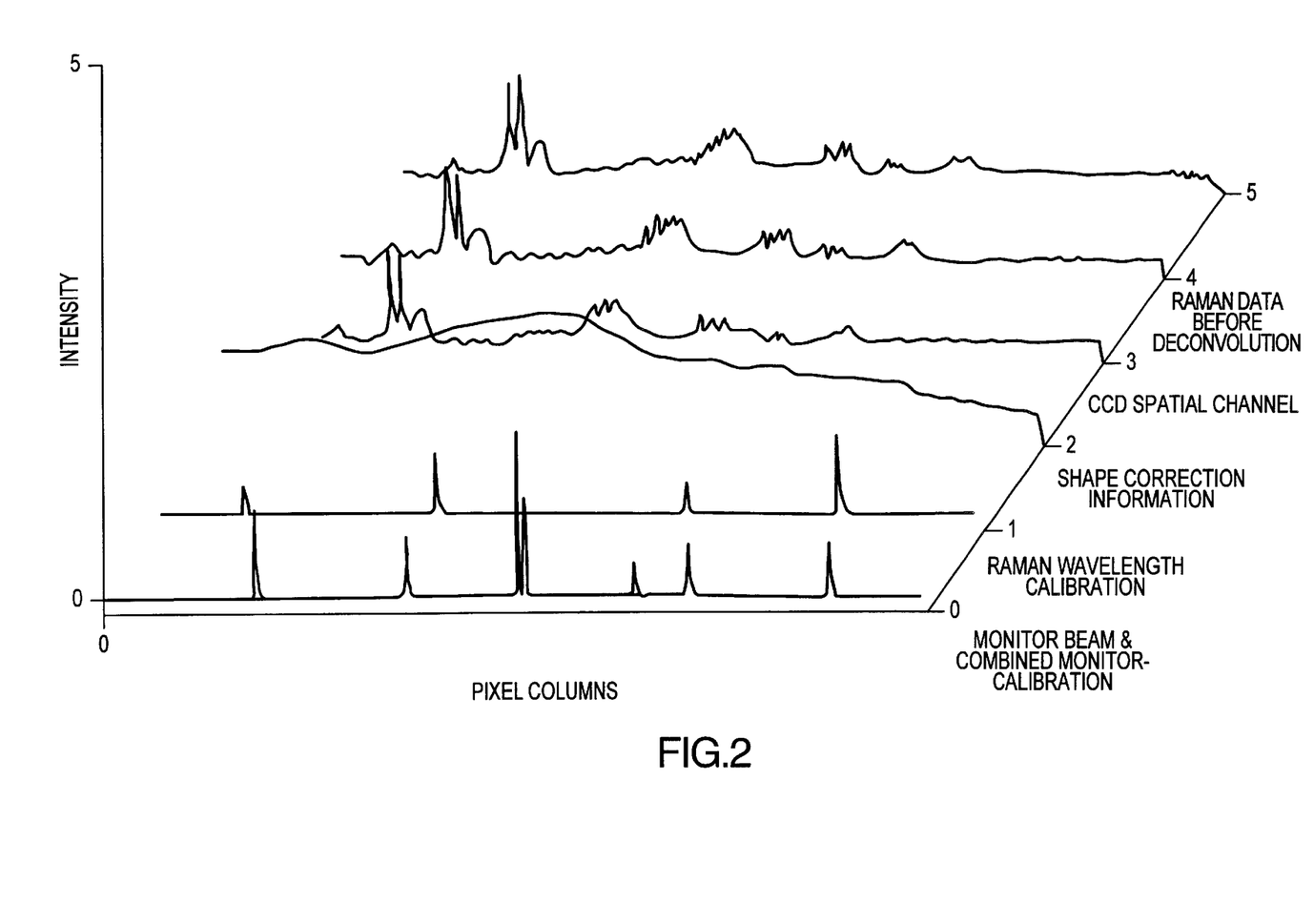
FIG. 2 is a graph showing an array of spectral data from a source of incident radiation.

The present invention also includes means for applying one or more integral transforms to Raman beam 32 and to monitor beam 24 spectral data thus collected, as shown by cross-reference among FIGS. 2–5. Equations for deconvolution are well known. As applied to the present invention, the equations may be applied to resulting spectral measurement data to produce the standard Raman spectrum of a sample. Deconvolution contributes to, but is not limited to, removal of unwanted frequency shifts and unwanted intensity changes of incident radiation 14. Autocorrelation methods, that may alternatively be applied to the Raman spectrum as shown in FIG. 2, may allow determination of the laser 16 spectral shape rather than measuring the spectral shape of laser 16 from combined monitor-calibration beam 68. The determined shape can subsequently be deconvolved from the raw Raman spectrum. Data collection in connection with integral transforms, in conjunction with the components of apparatus 10, combine to provide high resolution Raman spectra that are not dependent on frequency stability in source 12 of incident radiation 14, and are independent of intensity fluctuations associated with source of incident radiation 12. In addition, substantially simultaneous data measurements also allows user interchangeability of sample spectra among a number of spectrometers and similar apparatus because instrument variabilities are rendered irrelevant. Also, because corrections may be applied to correct for instrument variabilities, one or more multi-mode lasers not mode stabilized may be used as source 12 of incident radiation 14. In the preferred embodiment of the present invention laser 16 will not be stabilized, and will have the capability of having its frequency shifted by changes in temperature settings. In addition, the present invention permits taking spectral measurement prior to changing the frequency of laser 16 from one setting to a different setting, as well as after changing the frequency setting. Spectra of the sample and the monitor beam from each spectral measurement, before and after a frequency shift, may be subtracted from each other, and an integral transform applied to the resultant difference spectra. The resultant spectra will be corrected for common mode interferences as well as instrumentation variabilities, resulting in a standard Raman spectrum. As an additional result, more applications of the Raman principles are made possible, because a standard Raman spectrum is provided.

Figure 3:
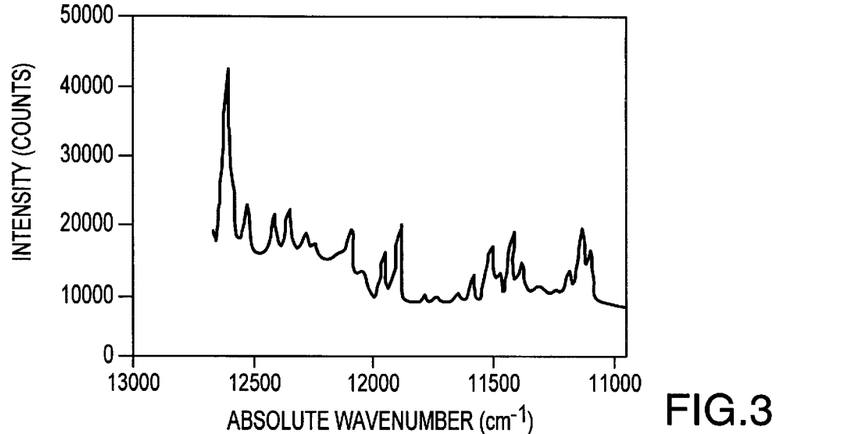
FIG. 3 is a graph showing spectral data associated with an incident beam obtained substantially simultaneously with the monitor beam data shown in FIG. 4.
Figure 4:
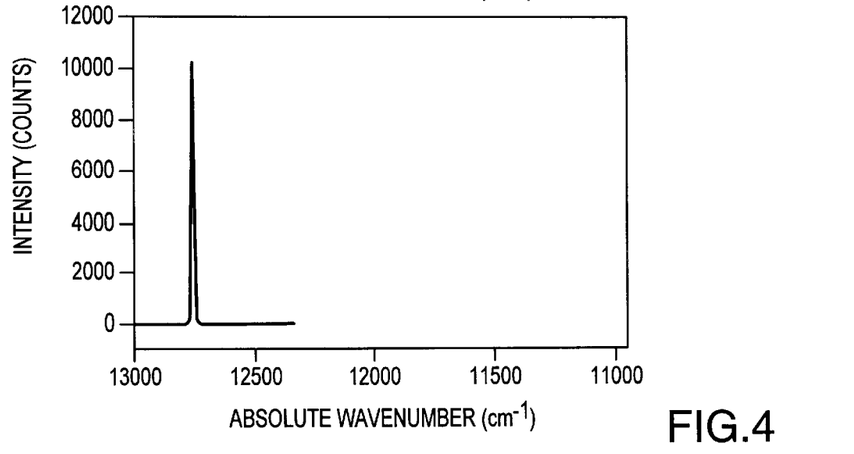
FIG. 4 is a graph showing spectral data associated with a monitor beam obtained substantially simultaneously with the data shown in FIG. 3.
Figure 5:
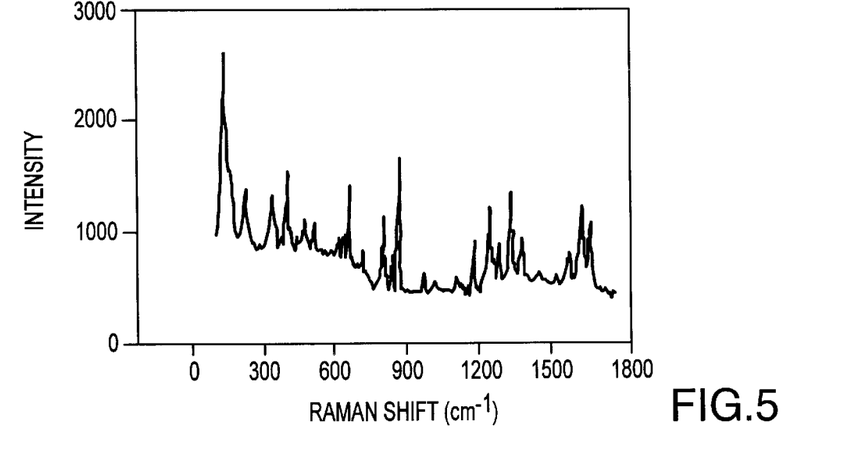
FIG. 5 is a graph showing spectral data associated with the Raman shift by application of one or more integral transforms to the spectral data.

Referring now by cross-reference among FIGS. 2–5, spectral data in connection with the present invention are provided. Shape correction for the resulting spectral data is shown and displayed as shown in FIG. 2. In addition, frequency calibration of the instrument may be displayed on a spatial channel as shown in FIG. 2. FIG. 2 includes a graph showing an array of spectral data obtained from a source of incident radiation in accordance with the present invention. FIG. 3 is a graph showing Raman spectral data associated with sample 26 obtained substantially simultaneously with the monitor beam spectral data shown in FIG. 4. FIG. 5 is a graph showing spectral data associated with the Raman shift by application of one or more integral transforms to the spectral data obtained in accordance with the present invention. As will be recognized by those skilled in the art, a computer or similar device may be used in conjunction with the apparatus for applying, and displaying the results of application, of the one or more integral transforms to the spectral measurements and to the resulting spectral measurement data.

While the particular method for adjusting spectral measurements to produce a standard Raman spectrum as shown and disclosed in detail in this instrument is fully capable of obtaining the objects and providing the advantages stated, this disclosure is merely illustrative of the presently preferred embodiments of the invention, and no limitations are intended in connection with the details of construction, design or composition other than as provided and described in the appended claims.

What is claimed is:

1. A method for adjusting spectral measurements to produce a standard Raman spectrum of a sample, comprising the steps of:
    selecting an apparatus for measuring and applying instrumentation correction to one or more beams of radiation, including an incident beam and a Raman beam;
    quantifying one or more frequency shifts in the incident beam and Raman beam;
    obtaining spectral data from the one or more beams of radiation; and
    applying one or more spectral data modifications to the spectral data to determine the standard Raman spectrum of a sample.

2. A method for adjusting spectral measurements to produce a standard Raman spectrum of a sample as recited in claim 1, wherein the selecting step includes the step of choosing a semiconductor laser as a source of the incident beam.

3. A method for adjusting spectral measurements to produce a standard Raman spectrum of a sample as recited in claim 1, wherein the quantifying step includes the substep of inducing one or more frequency shifts in the incident beam.

4. A method for adjusting spectral measurements to produce a standard Raman spectrum of a sample as recited in claim 1, wherein the quantifying step includes the substep of determining one or more frequency shifts in the incident beam.

5. A method for adjusting spectral measurements to produce a standard Raman spectrum of a sample as recited in claim 1, wherein the quantifying step includes the substep of measuring the one or more frequency shifts.

6. A method for adjusting spectral measurements to produce a standard Raman spectrum of a sample as recited in claim 1, wherein the obtaining step includes the substeps of:
    collecting spectral data from the incident beam and Raman beam substantially simultaneously;
    displaying data about the one or more frequency shifts on one or more graphs; and
    displaying the one or more graphs on a computer monitor.

7. A method for adjusting spectral measurements to produce a standard Raman spectrum of a sample as recited in claim 1, wherein the obtaining step includes the substep of directing the spectral data to a detector.

8. A method for adjusting spectral measurements to produce a standard Raman spectrum of a sample as recited in claim 1, wherein the obtaining step includes the substeps of:
    obtaining first spectral data from the incident beam;
    obtaining first spectral data from the Raman beam;
    confirming occurrence of a frequency shift in the incident beam and Raman beam;
    obtaining second spectral data from the incident beam; and
    obtaining second spectral data from the Raman Beam.

9. A method for adjusting spectral measurements to produce a standard Raman spectrum of a sample as recited in claim 1, wherein the applying step includes the substep of scaling.

10. A method for adjusting spectral measurements to produce a standard Raman spectrum of a sample as recited in claim 8, wherein the applying step includes the substeps of:
    subtracting the second spectral data from the incident beam from the first spectral data from the incident beam to provide a first result; and
    subtracting second spectral data from the Raman beam from the first spectral data from the Raman beam to provide a second result.

11. A method for adjusting spectral measurements to produce a standard Raman spectrum of a sample as recited in claim 10, wherein applying step includes the substep of applying one or more integral transforms to the first result and second result to produce the standard Raman spectrum of the sample.

12. A method for adjusting a spectral measurement to produce a standard Raman spectrum of a sample, comprising the steps of:
    selecting an apparatus for measuring and applying instrumentation correction to one or more beams of radiation, including an incident beam and a Raman beam;
    obtaining a spectral measurement set from the incident beam and Raman beam;
    shifting the spectral measurement set frequency axis to obtain one or more shifted spectral data sets; and
    applying one or more spectral data modifications to the spectral measurement set and one or more shifted spectral data sets to determine the standard Raman spectrum of a sample.

13. A method for adjusting a spectral measurement to produce a standard Raman spectrum of a sample as recited in claim 12, wherein the selecting step includes the substep of choosing a laser as a source of the incident beam.

14. A method for adjusting a spectral measurement to produce a standard Raman spectrum of a sample as recited in claim 12, wherein the obtaining step includes the substeps of:
    collecting spectral data from the incident beam and Raman beam substantially simultaneously;
    displaying data about the one or more frequency shifts on one or more graphs; and
    displaying the one or more graphs on a computer monitor.

15. A method for adjusting a spectral measurement to produce a standard Raman spectrum of a sample as recited in claim 12, wherein the shifting step may include the substeps of:
    mathematically altering the spectral measurement set; and
    altering the frequency axis of the apparatus.

16. A method for adjusting a spectral measurement to produce a standard Raman spectrum of a sample as recited in claim 15, wherein the shifting step may include the substep of performing a subsequent measurement to produce a second frequency shifted result.

17. A method for adjusting spectral measurements to produce a standard Raman spectrum of a sample as recited in claim 12, wherein the applying step includes the substeps of subtracting the spectral measurement set from the one or more shifted spectral data sets to produce a set of spectral differences.

18. A method for adjusting spectral measurements to produce a standard Raman spectrum of a sample as recited in claim 17, wherein the applying step includes the substep of flattening the set of spectral differences.

19. A method for adjusting spectral measurements to produce a standard Raman spectrum of a sample as recited in claim 18, wherein the applying step includes the substep of applying one or more integral transforms to the set of spectral differences to produce the standard Raman spectrum of the sample.

20. A method for producing a standard Raman spectrum of a sample, comprising the steps of:

selecting a source of incident radiation;

locating in the path of incident radiation means for providing an incident beam;

including one or more devices in the path of the incident beam for directing the incident beam at a sample;

installing adjacent the one or more devices means for generating a Raman beam from the sample;

providing means for substantially simultaneous collection of spectral data from the incident beam and Raman beam;

collecting one or more spectral measurements from one or more frequency shifts in the incident beam and one or more frequency shifts in the Raman beam;

obtaining first spectral data from the incident beam and from the Raman beam;

confirming occurrence of a frequency shift in the incident beam and Raman beam;

obtaining second spectral data from the incident beam and from the Raman Beam; and applying one or more spectral data modifications to the one or more spectral measurements to produce the standard Raman spectrum of the sample.

21. A method for producing a standard Raman spectrum of a sample as recited in claim 20, wherein the selecting step includes the substep of selecting a substantially monochromatic source of light.

22. A method for producing a standard Raman spectrum of a sample as recited in claim 20, wherein the locating step includes the substep of inducing one or more frequency shifts in the incident beam.

23. A method for producing a standard Raman spectrum of a sample as recited in claim 22, wherein the locating step includes the substep of identifying one or more frequency shifts in the incident beam.

24. A method for producing a standard Raman spectrum of a sample as recited in claim 20, wherein the collecting step includes the substeps of:

displaying data about the one or more frequency shifts on one or more graphs; and displaying the one or more graphs on a computer.

25. A method for producing a standard Raman spectrum of a sample as recited in claim 20, wherein the applying step may include the substep of scaling.

26. A method for producing a standard Raman spectrum of a sample as recited in claim 25, wherein the applying step includes the substeps of:

subtracting the second spectral data from the incident beam from the first spectral data from the incident beam to provide a first result; and subtracting second spectral data from the Raman beam from the first spectral data from the Raman beam to provide a second result.

27. A method for producing a standard Raman spectrum of a sample as recited in claim 26, wherein the applying step includes the substep of applying one or more integral transforms to the first result and second result to produce the standard Raman spectrum of the sample.

28. A method for adjusting one or more spectral measurements from a Raman beam to produce a standard Raman spectrum of a sample, comprising the steps of:

obtaining a first Raman spectral measurement;

collecting one or more subsequent Raman spectral measurements from an incident beam, the incident beam having a different wavelength from the first Raman spectral measurement; and applying one or more spectral data modifications to the spectral measurements to determine the standard Raman spectrum of a sample.

29. A method for adjusting one or more spectral measurements from a Raman beam to produce a standard Raman spectrum of a sample as recited in claim 28, wherein the obtaining step may include the substep of scaling.

30. A method for adjusting one or more spectral measurements from a Raman beam to produce a standard Raman spectrum of a sample as recited in claim 28, wherein the collecting step includes the substep of scaling.

31. A method for adjusting one or more spectral measurements from a Raman beam to produce a standard Raman spectrum of a sample as recited in claim 28, wherein the measuring step includes the substep of subtracting the one or more subsequent Raman spectral measurements from the first Raman spectral measurement to obtain one or more results.

32. A method for adjusting one or more spectral measurements from a Raman beam to produce a standard Raman spectrum of a sample as recited in claim 28, wherein the measuring step includes the substep of monitoring the incident beam substantially simultaneously with the Raman beam.

33. A method for adjusting one or more spectral measurements from a Raman beam to produce a standard Raman spectrum of a sample as recited in claim 28, wherein the measuring step includes the substep of applying one or more integral transforms to the one or more results to produce the standard Raman spectrum of the sample.

34. A method for adjusting one or more spectral measurements from a Raman beam to produce a standard Raman spectrum of a sample, comprising the steps of:

selecting a first Raman spectral measurement;

obtaining one or more Raman spectral data having a shifted frequency axis; and applying one or more spectral data modifications to the spectral data to determine the standard Raman spectrum of a sample.

35. A method for adjusting one or more spectral measurements from a Raman beam to produce a standard Raman spectrum of a sample as recited in claim 34, further comprising the substeps of subtracting the first Raman spectral measurement from the one or more Raman spectral data having a shifted frequency axis.

36. A method for adjusting one or more spectral measurements from a Raman beam to produce a standard Raman spectrum of a sample as recited in claim 34, further comprising the substeps of scaling the first Raman spectral measurement and the one or more Raman spectral data.

37. A method for adjusting one or more spectral measurements from a Raman beam to produce a standard Raman spectrum of a sample as recited in claim 34, further comprising the substeps of flattening any difference between the first Raman spectral measurement and the one or more Raman spectral data.

* * * * *